United States Patent [19]

Vince

[11] Patent Number: 5,265,604
[45] Date of Patent: Nov. 30, 1993

[54] DEMAND - DIAPHRAGMATIC PACING (SKELETAL MUSCLE PRESSURE MODIFIED)

[76] Inventor: Dennis J. Vince, 610 - 943 West Broadway, Vancouver, British Columbia V5Z 1K3, Canada

[21] Appl. No.: 54,606

[22] Filed: Apr. 30, 1993

Related U.S. Application Data

[63] Continuation of Ser. No. 522,708, May 14, 1990, abandoned.

[51] Int. Cl.$^5$ ............................................. A61N 1/36
[52] U.S. Cl. .................................................. 607/42
[58] Field of Search ................... 128/419 G, 421, 723

[56] References Cited

U.S. PATENT DOCUMENTS 4,827,936  5/1989  Geddes et al. ................. 128/419 G

OTHER PUBLICATIONS

"A heart-rate-responsive diaphragm pacemaker", Med. & Biol. Eng. & Comp., 1987, 25, 458-462, Kimura et al.

Primary Examiner—William E. Kamm
Assistant Examiner—Scott M. Getzow

[57] ABSTRACT

An apparatus to innervate diaphragms synchronously and to permit variation of the respiratory rate and duration in accordance with demand. The apparatus includes a sensor to sense skeletal muscle contraction and to produce a signal representative of the rate and intensity of muscle contraction at onset of inspiration. The signal can be modified in accordance with a predetermined pattern to provide a modified signal that is representative of a desired rate and duration of diaphragmatic contraction. A pulse generator is fed by the modified signal to produce a pulse. A stimulator is adapted to innervate the deinnervated lung diaphragms upon application of the pulse. A method of operating the apparatus to innervate both diaphragms is also disclosed.

5 Claims, 1 Drawing Sheet

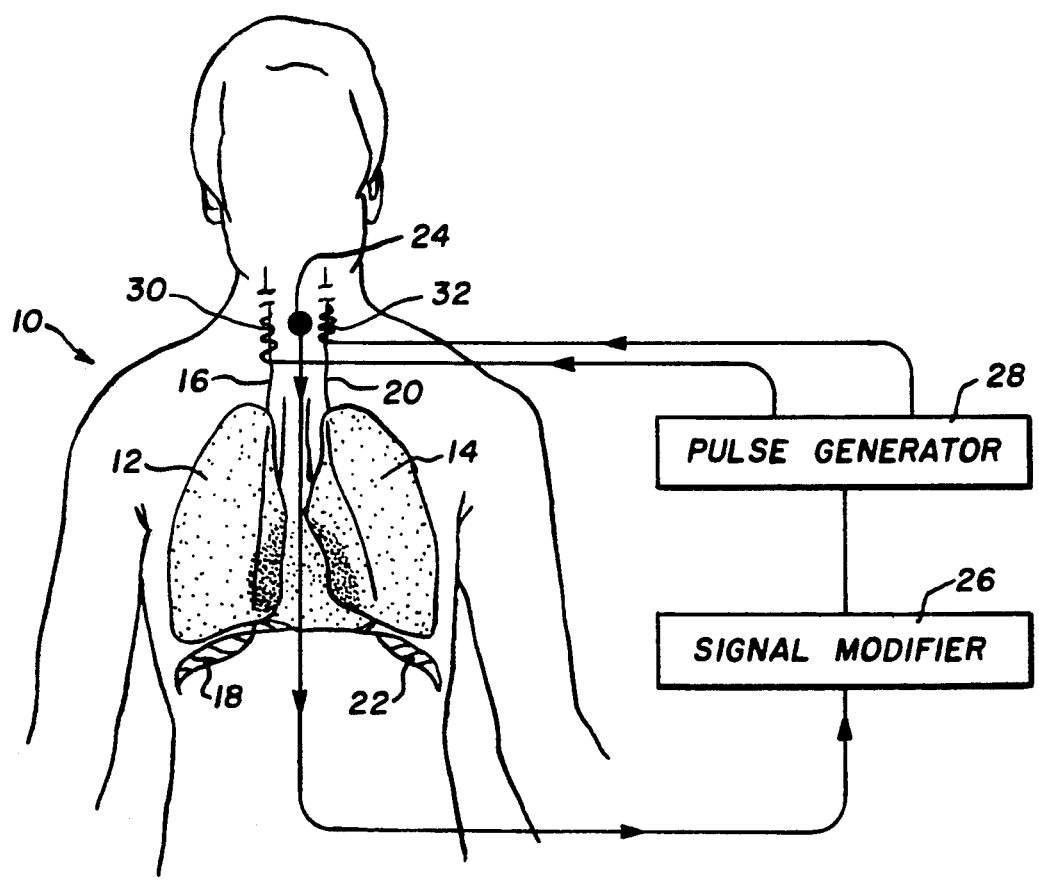

DEMAND - DIAPHRAGMATIC PACING (SKELETAL MUSCLE PRESSURE MODIFIED)

CROSS-REFERENCE TO RELATED APPLICATION

This is a continuation of application Ser. No. 07/522,708, filed May 14, 1990, now abandoned.

FIELD OF THE INVENTION

The present invention relates to a device for medical treatment of persons who as a result of trauma, surgical damage, acquired disease or congenital malformation have lost innervation of both diaphragms. More specifically, the present invention relates to a device to innervate both deinnervated diaphragms synchronously and to permit variation of the respiratory rate and duration in accordance with demand.

DESCRIPTION OF THE PRIOR ART

When both lung diaphragms have lost innervation due to trauma, surgical damage, acquired disease, congenital malformation or other reason, then the person generally requires artificial ventilation to remain alive. This is true when both diaphragms have lost innervation. When one diaphragm is deinnervated then the remaining innervated diaphragm can support life although ventilation is inefficient and the individual affected remains handicapped with reduced exercise capacity because of reduced ventilatory capacity.

It is known that electrical pacing of lung diaphragms can be carried out by producing an electrical stimulus which intermittently stimulates the diaphragmatic muscle to contract the diaphragm. The stimulus either occurs at the distal phrenic nerves or directly on the diaphragmatic muscles. In both cases the muscles of the diaphragm contract when stimulated appropriately and produce inspiration. This technology has shortcomings. The rate of pacing of the pulses to stimulate the diaphragms and the duration of the pacing per inspiration—which represents the respiratory rate and depth of inspiration-are fixed and do not vary with the physiological requirements of the body. As a person exercises, there is an increased oxygen demand and the respiratory rate of normal lung diaphragms increases. With fixed rate pacing the respiratory rate remains the same, as it is not physiologically regulated to vary the respiratory rate and duration when the oxygen and respiratory system demand increases or decreases.

SUMMARY OF THE INVENTION

It is an aim of the present invention to provide a system for innervating both diaphragms and to allow for variation in the rate and duration of synchronous diaphragmatic pacing in accordance with a person's requirement for increased or reduced respiratory system demand. A feedback loop is provided with a sensing device placed in the skeletal muscle which is innervated and contracts with the onset of normal inspiration and is under the command and direction of the central nervous system. This application is suitable for persons with bilateral deinnervation of the diaphragms, especially those with high spinal cord injury which can result in deinnervation of both phrenic nerves. In such patients, the cranial nerves which supply the skeletal muscles, palate and pharynx, remain innervated by the central nervous system. In this condition, the brain signals the need for inspiration, and the signal is received by the small skeletal muscles of the palate and the pharynx. The muscles contract to open the upper airway in anticipation of diaphragmatic contraction, and a rush of air enters from outside the body through the upper airway to enter the lungs. However, the signal creating diaphragmatic contraction is interrupted by the spinal cord injury and is not received. The diaphragms do not contract and no inspiration occurs. Such a person would die of respiratory failure unless a mechanical respiratory or a bilateral diaphragmatic pacer was operational in order to induce inspiration. However, the known diaphragmatic pacers are such that respiration proceeds at a fixed rate not necessarily related to the physiological requirements of the patient.

Whereas the present invention provides a muscle sensing device to produce a signal from the skeletal muscle representative of muscle contraction at the onset of, inspiration, my co-pending application Ser. No. 07/522,778 filed concurrently with the present application discloses a temperature sensing device to sense the colder air entering the thorax during inspiration. This technology will be employed only if one of the diaphragms is innervated. The signal will be used to synchronize the contraction of the other, non-innervated diaphragm. In the case of unilateral diaphragmatic paralysis the normally innervated diaphragm is regulated in its rate and duration by the central nervous system. Therefore the deinnervated diaphragm, which is tracking and following the innervated diaphragm, comes under physiological regulation from the central nervous system of the patient. Therefore no algorithm is required to modify rate and duration in the case of unilateral diaphragmatic paralysis. Furthermore, my co-pending application Ser. No. 07/522,779 filed concurrently with the present application discloses a system of innervating lung diaphragms from a signal modified from an electrocardiogram pick up.

The present invention provides an apparatus to innervate both deinnervated diaphragms and permit variation of the respiratory rate and duration in accordance with demand, comprising muscle contraction sensing means adapted to sense skeletal muscle contraction and produce a signal representative of rate and intensity of muscle contraction at onset of inspiration, means to modify the signal in accordance with a predetermined pattern to provide a modified signal representative of desired rate and duration of diaphragmatic contraction, pulse generator means fed by the modified signal to produce a pulse, and stimulating means adapted to innervate both deinnervated diaphragms upon application of the pulse.

The present invention also provides a method of operating an apparatus to innervate both deinnervated lung diaphragms and permit variation of the respiratory rate and duration in accordance with demand, comprising the steps of sensing skeletal muscle contraction and producing a signal representative of rate and intensity of muscle contraction at onset of inspiration, modifying the signal in accordance with a predetermined pattern to provide a modified signal representative of desired rate and duration of diaphragmatic contraction, utilizing the modified signal with a pulse generator means to produce a pulse, and feeding the pulse to a stimulating means adapted to innervate both deinnervated lung diaphragms.

DESCRIPTION OF THE DRAWING

The figure is a schematic view of one embodiment of the apparatus according to the present invention.

DESCRIPTION OF THE PREFERRED EMBODIMENT

A body 10 is shown in the figure with a normal innervated right lung diaphragm 12 and a deinnervated left lung diaphragm 14. The right diaphragm distal phrenic nerve 16 stimulates the diaphragmatic muscle 18 to contract the right diaphragm 12. Similarly the left diaphragm distal phrenic nerve 20 stimulates the diaphragmatic muscle 22 to contract the left diaphragm 14. A pressure sensor 24 is shown buried within the skeletal muscle of the pharyngeal muscles. The pressure sensor 24 produces a signal sensing the onset of inspiration and also the intensity of muscle contraction, and sends the signal to a signal modifier 26 where it is modified in accordance with a predetermined pattern, which may be an adjustable algorithm, to generate a modified signal for feeding to a pulse generator 28. As shown in the figure, the pulse generator 28 passes a pulse to electrodes shown in the form of subcutaneous induction coils 30 and 32 around the skeletal phrenic nerves 16 and 20 or alternatively to both the diaphragmatic muscles 18 and 22 to produce diaphragmatic contractions.

In operation the central nervous system modifies the frequency of inspiration dependent upon the physiological needs of the person, and determines the rate and intensity of contraction for the innervated muscles in the pharynx. The onset of contraction is sensed by the pressure sensor 24 as well as the intensity of contraction and this is signalled to the signal modifier 26. The modification takes into account a predetermined pattern for rate and duration of innervation and a modified signal is passed to the pulse generator 28 which in turns sends a pulse to the electrodes to produce diaphragmatic contraction.

The pulse generator 28 can be placed outside the body and have an external induction coil to feed pulses to the subcutaneous induction coils 30 and 32 about the phrenic nerves or directly to the diaphragmatic muscle within the body. The system operates bilaterally when both diaphragms are deinnervated.

Various changes may be made to the embodiment shown herein without departing from the scope of the present invention which is limited only by the following claims.

The embodiments of the present invention in which an exclusive property or privilege is claimed are defined as follows:

1. An apparatus to innervate both deinnervated diaphragms of a patient synchronously and permit variation of the respiratory rate and duration in accordance with demand, comprising:
   muscle contraction sensing means adapted to sense pharyngeal muscle contraction within the pharynx at the onset of inspiration and the intensity of the muscle contraction, and produce a signal representative of rate and intensity of pharyngeal muscle contraction at onset of inspiration,
   means to modify the signal in accordance with a predetermined pattern to provide a modified signal representative of desired rate and duration of diaphragmatic contraction,
   pulse generator means fed by the modified signal to produce a pulse, and
   stimulating means adapted to innervate both deinnervated diaphragms upon application of the pulse.

2. The apparatus according to claim 1 wherein the pulse generator means comprises an electrical pulse wave generator providing an electrical pulse to the stimulating means for producing intermittent contractions to both diaphragms at predetermined rates and durations.

3. The apparatus according to claim 1 wherein the means to modify the signal in accordance with a predetermined pattern is adjustable dependent upon the rate and intensity of the signal received from the pharyngeal muscle contraction sensing means.

4. The apparatus according to claim 1 wherein the stimulating means comprise subcutaneous induction coils adapted for surrounding the distal phrenic nerves.

5. A method of operating an apparatus to innervate both deinnervated diaphragms of a patient and permit variation of the respiratory rate and duration in accordance with demand, comprising the steps of
   sensing pharyngeal muscle contraction within the pharynx at the onset of inspiration and the intensity of the muscle contraction and producing a signal representative of a rate and intensity of pharyngeal muscle contraction at onset of inspiration,
   modifying the signal in accordance with a predetermined pattern to provide a modified signal representative of desired rate and duration of diaphragmatic contraction,
   utilizing the modified signal with a pulse generator means to provide a pulse, and
   feeding the pulse to a stimulating means adapted to innervate both diaphragms.

* * * * *